US011517330B2

(12) United States Patent
Souryal

(10) Patent No.: US 11,517,330 B2
(45) Date of Patent: Dec. 6, 2022

(54) PREGNANT GUIDE PIN DRILL PASSER

(71) Applicant: Tarek O. Souryal, Dallas, TX (US)

(72) Inventor: Tarek O. Souryal, Dallas, TX (US)

( * ) Notice: Subject to any disclaimer, the term of this patent is extended or adjusted under 35 U.S.C. 154(b) by 394 days.

(21) Appl. No.: 16/724,013

(22) Filed: Dec. 20, 2019

(65) Prior Publication Data

US 2020/0197029 A1 Jun. 25, 2020

Related U.S. Application Data

(60) Provisional application No. 62/784,096, filed on Dec. 21, 2018.

(51) Int. Cl.
| *A61B 17/16* | (2006.01) |
| *A61B 17/17* | (2006.01) |
| *A61B 17/04* | (2006.01) |
| *A61B 17/00* | (2006.01) |

(52) U.S. Cl.
CPC .......... *A61B 17/17* (2013.01); *A61B 17/1615* (2013.01); *A61B 2017/00862* (2013.01); *A61B 2017/0414* (2013.01)

(58) Field of Classification Search
CPC ......... A61B 17/1714; A61B 17/1615–17/1633
See application file for complete search history.

(56) References Cited

U.S. PATENT DOCUMENTS

| 5,601,550 A * | 2/1997 | Esser ................. A61B 17/6433 606/54 |
| 5,941,706 A * | 8/1999 | Ura ......................... A61C 3/02 433/165 |
| 8,777,949 B2 | 7/2014 | Ranck et al. |
| 9,186,156 B2 | 11/2015 | Xie |
| 10,022,131 B1 * | 7/2018 | Burley ............... A61B 17/1631 |
| 10,070,870 B2 | 9/2018 | Lu et al. |
| 10,245,044 B2 | 4/2019 | Petersen |
| 10,702,289 B2 * | 7/2020 | Saw ................... A61B 17/1675 |
| 10,856,889 B1 * | 12/2020 | Burley ............... A61B 17/1664 |
| 2008/0188935 A1 * | 8/2008 | Saylor ................ A61B 17/0401 623/13.14 |
| 2009/0209964 A1 | 8/2009 | Yeung |
| 2010/0286694 A1 * | 11/2010 | Rio .................... A61B 17/1617 606/80 |
| 2011/0208194 A1 * | 8/2011 | Steiner ............... A61B 17/1764 606/80 |
| 2012/0116534 A1 | 5/2012 | Forsell |
| 2012/0211280 A1 | 8/2012 | Dewey et al. |
| 2015/0066036 A1 | 3/2015 | McGinley et al. |
| 2016/0022339 A1 | 1/2016 | Machida |
| 2016/0166260 A1 | 6/2016 | Ellis |
| 2018/0084985 A1 * | 3/2018 | Saw ................... A61B 17/1675 |
| 2019/0262007 A1 | 8/2019 | Ellis |

* cited by examiner

*Primary Examiner* — Zade Coley

(57) ABSTRACT

This disclosure provides an apparatus, system and method for pregnant guide pin drill passer. The pregnant guide pin drill passer includes a drill shank removably to transfer a rotational force of a drill; a drill neck to translate the rotational force from the drill shank to the drill bit; the drill bit to use the rotational force to create a bone tunnel in a bone; a hole finisher to embed bone dust into a surface of the bone tunnel; an eyelet to receive a first end of a suture after the drill shank is removed from the drill, pull the first end of the suture through the bone tunnel when the drill shank is pulled through the bone tunnel, and remove the suture from the eyelet.

3 Claims, 4 Drawing Sheets

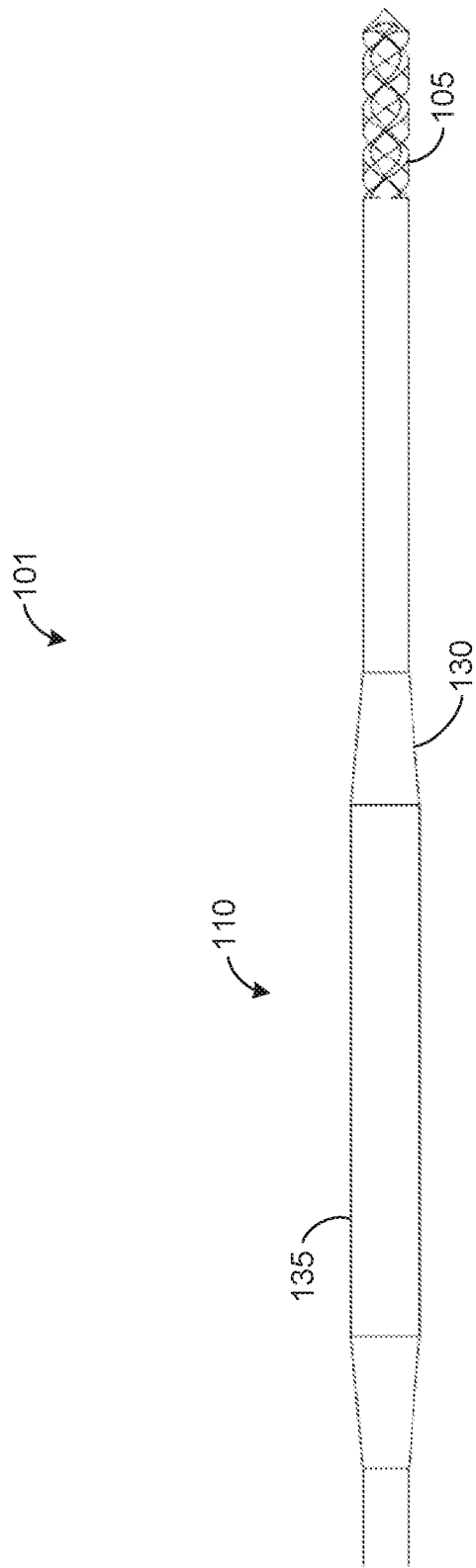
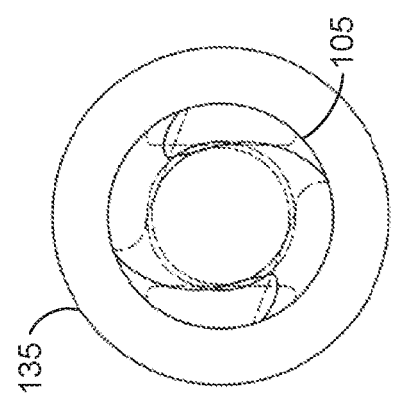
FIGURE 1B
FIGURE 1C

US 11,517,330 B2

PREGNANT GUIDE PIN DRILL PASSER

CROSS-REFERENCE TO RELATED APPLICATIONS

This application claims priority to U.S. Provisional Patent Application Ser. No. 62/784,096 entitled PREGNANT GUIDE PIN DRILL PASSER and filed on Dec. 21, 2018. The content of the above-identified patent documents is hereby incorporated by reference.

TECHNICAL FIELD

This invention relates in general to surgical devices, more particularly, to an apparatus for a pregnant guide pin drill passer.

BACKGROUND

Surgeries are important procedures for maintaining simplicity and reducing clutter in a small area. For implants, creating a hole in a bone for the implant to be set requires a number of different pieces of equipment for drilling the hole, enlarging the hole, cleaning the hole, and running implants through the hole. The components for each of these procedures need to be close and available for use as the need arises, which could cause a problem if a specific tool is misplaced or broken.

SUMMARY

This disclosure provides a pregnant guide pin drill passer and related methods.

In a first embodiment, a pregnant guide pin drill passer meant to pass through a hole that is created is provided. The pregnant guide pin drill passer includes a drill shank removably attached to transfer a rotational force of a drill; a drill neck to translate the rotational force from the drill shank to the drill bit; the drill bit to use the rotational force to create a bone tunnel in a bone; a hole finisher to embed bone dust into a surface of the bone tunnel; an eyelet to receive a first end of a suture after the drill shank is removed from the drill, pull the first end of the suture through the bone tunnel when the drill shank is pulled through the bone tunnel, and remove the suture from the eyelet.

In a second embodiment, a method for using a pregnant guide pin drill passer is provided. The method includes removeably attaching a drill shank to a drill to receive a rotational force from the drill; transmitting the rotational force to through a drill neck from the drill shank to a drill bit; creating a bone tunnel in a bone using the drill bit using the rotational force; embedding bone dust into a surface of the bone tunnel using a hole finisher; removing the drill shank from the drill when the hole finisher exits the bone tunnel; inserting a first end of a suture into the eyelet; pulling the eyelet with the first end of the suture through the bone tunnel; and removing the suture from the eyelet.

In a second embodiment, a method for using a pregnant guide pin drill passer is provided. The method includes receiving, by a drill shank of the pregnant guide pin drill passer, a rotational force from a drill, wherein the drill shank is removably attached to the drill; transmitting the rotational force to through a drill neck from the drill shank to a drill bit; creating a bone tunnel in a bone using the drill bit using the rotational force; embedding bone dust into a surface of the bone tunnel using a hole finisher; removing the drill shank from the drill when the hole finisher exits the bone tunnel; receiving a first end of a suture into the eyelet; pulling the eyelet with the first end of the suture through the bone tunnel; and releasing the suture from the eyelet.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; and the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts:

FIGS. 1A-1E illustrate an example pregnant guide pin drill passer according to this disclosure.

DETAILED DESCRIPTION

Figure 1A:
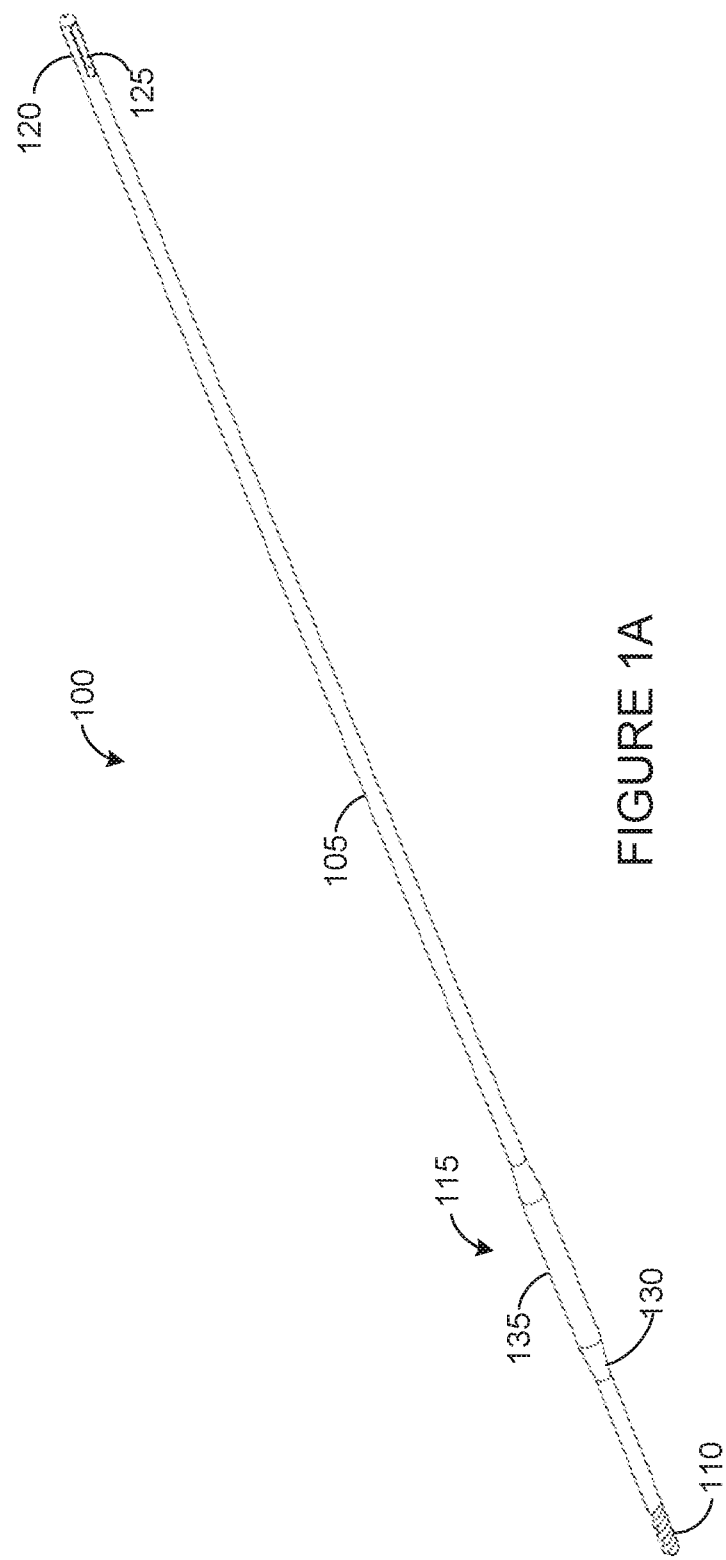
Figure 1D:
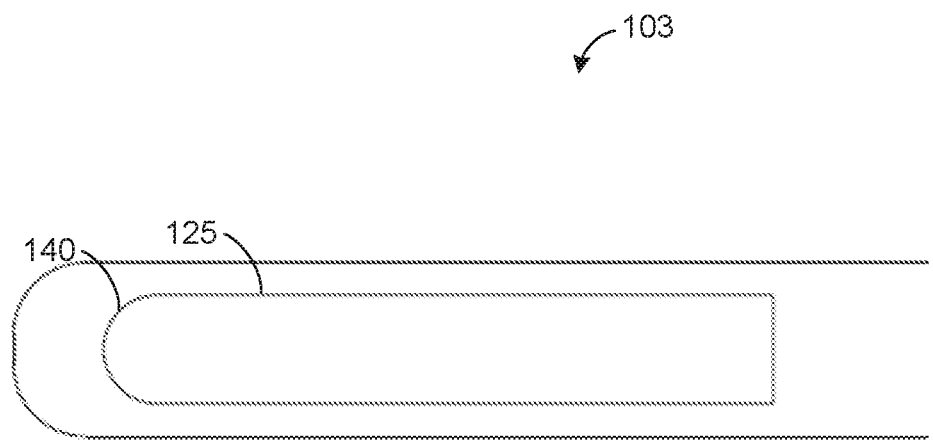
Figure 1E:
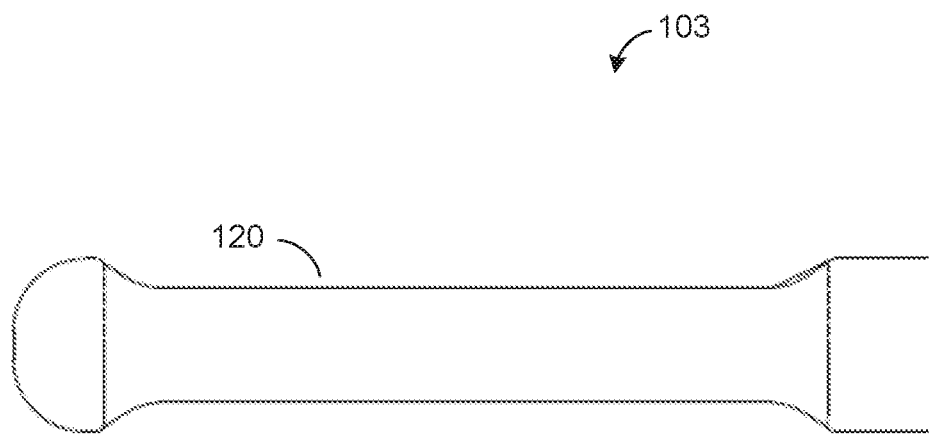
Figure 2:
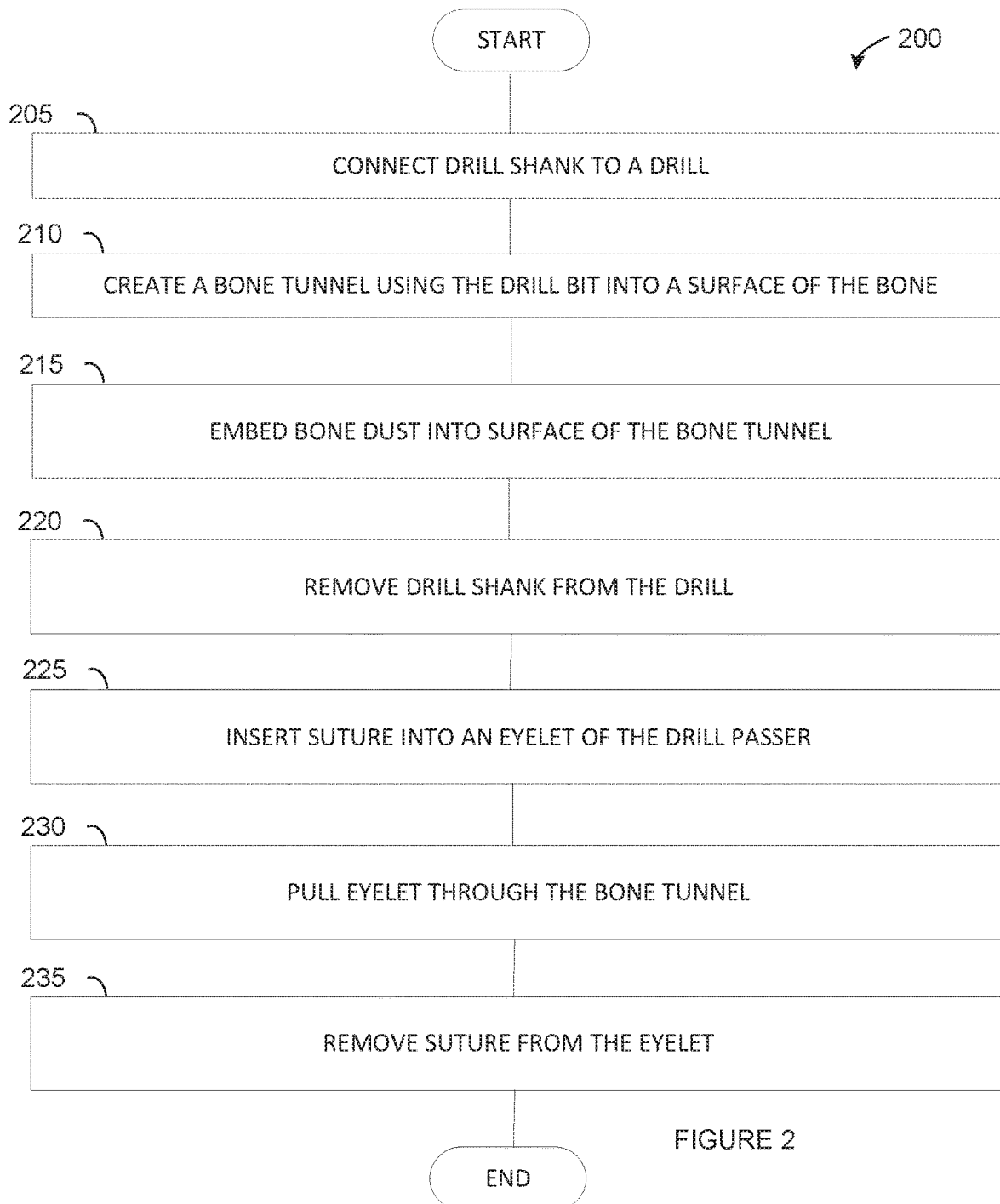
FIG. 2 illustrates an example of using a pregnant guide pin drill passer according to this disclosure.

FIGS. 1A through 2, discussed below, and the various embodiments used to describe the principles of the present disclosure in this patent document are by way of illustration only and should not be construed in any way to limit the scope of the disclosure.

FIGS. 1A-1E illustrate an example pregnant guide pin drill passer 100 according to this disclosure. Pregnant is defined as a function of a second enlargement of hole to occur after the initial drilling enlargement. FIG. 1A illustrates a pregnant guide pin drill passer 100 according to the various embodiments of the present disclosure. FIG. 1B illustrates a front end 101 of the pregnant guide pin drill passer 100. FIG. 1C illustrates a front view 102 of the pregnant guide pin drill passer 100. FIG. 1D illustrates a first view of a back end 103 of the pregnant guide pin drill passer 100. FIG. 1E illustrates a second view of the back end 103 of the pregnant guide pin drill passer 100. The embodiments of the pregnant guide pin drill passer 100 illustrated in FIGS. 1A-1E are for illustration only. FIGS. 1A-1E do not limit the scope of this disclosure to any particular implementation of a pregnant guide pin drill passer.

The pregnant guide pin drill passer 100 is an orthopedic tool to be used to place, drill and expand a specialized tunnel within bones, while minimizing bone dust. The special configuration of this all-in-one tool allows for a sequential drilling, expanding and compressing the cancellous bone of the femur, tibia, humerus, calcaneus etc. In addition, pregnant guide pin drill passer 100 also uses the eyelet to pass suture or other devices. The drill passer 100 is preferably made of specialized metal that is flexible, resilient, hypoallergenic, and strong to avoid breakage, such as, but not limited to, a titanium alloy. The pregnant guide pin drill passer 100 includes a drill neck 105, a partial drill bit 110, a hole finisher 115, a drill shank 120, and an eyelet 125.

The drill neck 105 extends a length suitable for a surgical procedure. For example, a length of the drill neck 105 allows the expander 130 to clear through a medium, such as bone, being drilled. In other words, expander 130 would completely pass through a tunnel created in the bone before a drill connected to the drill shank 120 would be interfered with by the bone itself. The drill neck 105 has a firmness that provides a straight tunnel in the bone. The firmness of the drill neck 105 is defined by the rotational flexibility and the bending flexibility. As the drill passer 100 is an overall small diameter instrument, the bending moments and the rotational moments need to be minimized. The material chosen for the body can be different from a material of the drill bit 110 and the hole finisher 115.

The partial drill bit 110 located at a first end of the drill neck. The partial drill bit 110 can drill a hole in bone and can pull the passer through the hole. The partial drill bit 110 is partially threaded. The partial threading of the drill bit 110 allows for other components increase the functionality of the drill passer 100. As the drill bit 110 is drilling a tunnel through the bone, parts of the bone are compressed outwards in relation to the drill bit and other parts are shaved off. These bits will be referred to as "bone dust." The bone dust created by the drill bit 110 is to be minimized. The type of drill bit 110 can be based on the type of bone to be drilled into, such as bone density, bones thickness, etc.

The hole finisher 115 located at the first end of the drill neck at a distance inside the partial drill bit. The hole finisher includes an expander 130 and a presser 135. The hole finisher 115 purpose is to make sure that bone dust or bone shavings from the partial drill bit 110 do not get exposed in the body outside the bone. The portion of drill passer 100 between the drill bit 110 and the hole finisher 115 has a diameter that is equal to or less than the end of the drill bit 110. This portion can be the same diameter and strength as the drill neck 105 or a reduced diameter with similar strength.

The expander 130 can expand a diameter of the hole. The expander 130 is a transition of the diameter from the drill neck 105 to the presser 135. The transition of the expander 130 can be constant or variable. For instance, the variable transition can be greater at the beginning of the transition from the drill neck 105 than the end of the transition at the presser 135. The end of the expander 130 has a diameter that is slightly greater than the largest diameter of the drill bit.

The presser 135 located after the expander and has a diameter larger than a diameter of the drill neck 105. The presser 135 can force bone dust from the partial drill bit 110 into a side wall of the hole in the bone. The presser 135 also can be used as a supplemental support to keep the drill bit 110 in alignment. As the bone tunnel is being created by the drill bit 110, the presser 135 provides additional support for the alignment of the drill bit 110. Thus, any sudden or wavering movement at the drill will be reduced. The presser 135 can have a slight increase in diameter from the front end of the drill passer 100 to the back end of the drill passer 100. The outward rotational force generated from the drill is transmitted to the drill bit 110 through the drill neck 105 and the hole finisher 115. Thus, the rotational force of the drill applied on the bone tunnel by the presser 135 causes the bone dust to be embedded in the surrounding bone.

The drill shank 120 located at a second end of the drill neck 105 that is opposite to the drill bit 110 at the first end. The drill shank 120 is can be gripped by a drill. The shape of the drill shank 120 is conducive for a standard drill to grip the pregnant guide pin drill passer 100. As a perfect circle would primarily depend on friction for the drill maintaining a grip on the drill passer 100, the drill shank 120 can include one or more flat or textured surface. The drill shank 120 could also be structured as a specialized shape for connecting to a specialized drill.

The eyelet 125 located at a second end of the drill neck 105. The eyelet can hold a suture or other surgical thread. The eyelet 125 can be located inside of the drill neck 105 within the drill shank 120 portion. Typically, the suture or other surgical thread is threaded through the eyelet 125 after the hole finisher 115 has exited the tunnel created in the bone. The eyelet 125 could also be used as an additional surface for the drill to clasp onto while producing the bone tunnel. The eyelet 125 can have a transitional curve 140 at the back end of the drill presser 100. The transitional curve is a rounded surface of the eyelet that smoothly transition into the surface of the drill shank 120 to not form any edges. In other words, the transitional curve 140 of the eyelet 125 would be free from any edges to not cause any damage or rubbing of the suture or other surgical threads.

FIG. 2 illustrates an example of using a pregnant guide pin drill passer 100 according to this disclosure. For example, the process depicted in FIG. 2 may be performed by the drill passer 100 illustrated in FIGS. 1A-1E.

In operation 205, a drill bit 120 is connected to the drill. The drill shank 120 is structured with an indented or flat surface for mating with the drill. The drill bit 120 translates the rotational force from the drill to the drill bit 110 through the drill neck 105.

In operation 210, the drill bit 110 creates a bone tunnel into the bone. The drill bit 110 is applied to the surface of a bone. A rotational force of the drill is used to cause the drill bit 110 to be pulled through the bone. The drill bit 110 creates an initial sized tunnel and can generate bone dust as a byproduct of the bone tunnel formation. The amount of bone dust is minimized by the shape of length of the drill bit 110. The drill bit 110 is a partial drill bit in that the drill portion extends only along a portion of the drill neck 105.

The drill passer 100 includes a hole finisher 115 that expands the bone tunnel and embeds any bone dust generated into the surface of the bone tunnel. The hole finisher 115 includes an expander 130 and a presser 135. The expander 130 is a transitional section between the drill bit 110 and the presser 135 that causes further expansion of the bone tunnel. The expander 130 is pulled by the drill bit 110 to cause the bone tunnel to increase in diameter. The presser 135 can stabilize the drill bit 110 both before entering the bone tunnel and inside the bone tunnel. The presser 135 can be lightly gripped or be entered into an external guide for aligning the drill bit 110. For example, the length of the presser 135 can align with the surface of the bone tunnel ensuring alignment of the drill bit for any radical movement or rotation at the drill. In other words, the movement or rotation of the drill can be muted or reduced by the stabilizing of the presser.

In operation 215, the hole finisher 115 embeds bone dust into the surfaces of the bone tunnel. After the tunnel is expanded, the presser 135 exerts force on the surface of the expanded bone tunnel. Any bone dust that is generated can be pressed by the presser 135 into the surface of the bone tunnel.

In operation 220, the drill shank 120 is removed from the drill. Once the hole finisher 115 is completely through the bone tunnel and exposed on the opposite side of the bone, the drilling is completed. The drill passer 100 remains in a position where an eyelet 125 is on one side of the bone and the hole finisher is on the other side of the bone. In other words, the drill neck 105 remains in the bone tunnel.

In operation 225, a suture is inserted into an eyelet 125 of the drill passer 100. When the hole finished 115 is completely through the bone tunnel and the drill has been removed, the eyelet 125 is used to thread a suture or other surgical thread. The side of the eyelet closest to the second end is rounded with respect to the drill shank 120 and with respect to the hole. The rounded surface ensures that the suture will not experience rubbing or damage that might affect the suture itself.

In operation 230, the eyelet is pulled through the bone tunnel with the suture. The drill passer 100 at this point is completely through the bone tunnel with the suture being drawn through. The suture has one end out of each end of the bone tunnel. In operation 235, the suture is removed from the eyelet 125.

Although FIG. 2 illustrates an example of using a pregnant guide pin drill passer, various changes could be made to FIG. 2. For example, while shown as a series of steps, various steps in each figure could overlap, occur in parallel, occur in a different order, or occur multiple times.

Although the present disclosure has been described with exemplary embodiments, various changes and modifications may be suggested to one skilled in the art. It is intended that the present disclosure encompass such changes and modifications as fall within the scope of the appended claims.

What is claimed is:

1. A pregnant guide pin drill passer comprising:
   a drill shank configured to be removably attached to a drill to transfer a rotational force;
   a drill neck connected to the drill shank and a drill bit and configured to translate the rotational force from the drill shank to the drill bit;
   the drill bit attached at an end of the drill neck and configured to use the rotational force to create a bone tunnel in a bone;
   a hole finisher located on the drill neck between the drill shank and the drill bit, the hole finisher configured to embed bone dust into a surface of the bone tunnel, wherein the hole finisher includes:
      a presser that is a greater diameter than a diameter of the drill neck and is a greater diameter than a diameter of the drill bit, and
      an expander at a side of the hole finisher closest to the drill bit and configured to expand a diameter of the bone tunnel, wherein the expander is structured as a transition between a diameter of the drill neck and a diameter of the presser with a variable sloped transition that reduces from a side closer to the drill bit towards a side closer to the drill shank, wherein the diameter of the presser at a side towards the drill shank is larger than the diameter of the presser at a side towards the drill bit, wherein the diameter of the drill neck between the presser and the drill shank is less than the diameter of the presser; and
   an eyelet structured with rounded edges and located at the drill shank, the eyelet configured to:
      receive a first end of a suture after the drill shank is removed from the drill,
      pull the first end of the suture through the bone tunnel when the drill shank is pulled through the bone tunnel, and
      remove the suture from the eyelet,
   wherein the drill neck is structured to extend a length where the drill shank and the presser would be on opposite ends of a bone through the bone tunnel.

2. A method for using pregnant guide pin drill passer, the method including:
   removeably attaching a drill shank to a drill to receive a rotational force from the drill;
   transmitting the rotational force to through a drill neck from the drill shank to a drill bit;
   creating a bone tunnel in a bone using the drill bit using the rotational force;
   embedding bone dust into a surface of the bone tunnel using a hole finisher located on the drill neck between the drill shank and the drill bit, wherein the hole finisher includes:
      a presser that is a greater diameter than a diameter of the drill neck and a diameter of the drill bit, and
      an expander at a side of the hole finisher closest to the drill bit and configured to expand a diameter of the bone tunnel, wherein the expander is structured as a transition between a diameter of the drill neck and a diameter of the presser with a variable sloped transition that reduces from a side closer to the drill bit towards a side closer to the drill shank, wherein the diameter of the presser at a side towards the drill shank is larger than the diameter of the presser at a side towards the drill bit, wherein the diameter of the drill neck between the presser and the drill shank is less than the diameter of the presser;
   removing the drill shank from the drill when the hole finisher exits the bone tunnel, wherein the drill neck is structured to extend a length where the drill shank and the presser would be on opposite ends of a bone through the bone tunnel;
   inserting a first end of a suture into an eyelet structured with rounded edges and located at the drill shank;
   pulling the eyelet with the first end of the suture through the bone tunnel; and
   removing the suture from the eyelet.

3. A method performed by a pregnant guide pin drill passer, the method including:
   receiving, by a drill shank of the pregnant guide pin drill passer, a rotational force from a drill, wherein the drill shank is removably attached to the drill;
   transmitting the rotational force to through a drill neck from the drill shank to a drill bit;
   creating a bone tunnel in a bone using the drill bit using the rotational force;
   embedding bone dust into a surface of the bone tunnel using a hole finisher located on the drill neck between the drill shank and the drill bit, wherein the hole finisher includes:
      a presser that is a greater diameter than a diameter of the drill neck and a diameter of the drill bit, and
      an expander at a side of the hole finisher closest to the drill bit and configured to expand a diameter of the bone tunnel, wherein the expander is structured as a transition between a diameter of the drill neck and a diameter of the presser with a variable sloped transition that reduces from a side closer to the drill bit towards a side closer to the drill shank, wherein the diameter of the presser at a side towards the drill shank is larger than the diameter of the presser at a side towards the drill bit, wherein the diameter of the drill neck between the presser and the drill shank is less than the diameter of the presser;
   removing the drill shank from the drill when the hole finisher exits the bone tunnel wherein the drill neck is structured to extend a length where the drill shank and the presser would be on opposite ends of a bone through the bone tunnel;

receiving a first end of a suture into an eyelet structured with rounded edges and located at the drill shank;

pulling the eyelet with the first end of the suture through the bone tunnel; and releasing the suture from the eyelet.

* * * * *